(12) United States Patent
Brahmachari et al.

(10) Patent No.: US 6,764,824 B2
(45) Date of Patent: Jul. 20, 2004

(54) PRIMERS FOR SCREENING SCHIZOPHRENIA AND A METHOD THEREOF

(75) Inventors: Samir Kumar Brahmachari, Delhi (IN); Ranjana Verma, Delhi (IN); Chitra Chauhan, Delhi (IN); Salim Quaiser, Delhi (IN); Sanjeev Jain, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/104,869

(22) Filed: Mar. 21, 2002

(65) Prior Publication Data

US 2003/0180730 A1 Sep. 25, 2003

(51) Int. Cl.[7] .................... C12Q 1/68; C12P 19/34; C07H 21/04
(52) U.S. Cl. ................ 435/6; 435/91.2; 435/91.1; 536/23.1; 536/24.3; 536/24.33
(58) Field of Search .................. 435/6, 91.1, 91.2, 435/810; 536/24.33, 24.3, 23.1

(56) References Cited

PUBLICATIONS

Meyer et al. A missense mutatuon in a novel gene ecndoing a putative cation channel is associated with catatonic shizophrenia in a large pedigree. Molecular Psychiatry, vol. 6, pp. 302–306, Mar. 19, 2001.*

* cited by examiner

*Primary Examiner*—Kenneth R. Horlick
*Assistant Examiner*—Cynthia Wilder
(74) *Attorney, Agent, or Firm*—John P. White; Cooper & Dunham LLP

(57) ABSTRACT

The present invention relates to novel primers useful for identifying and screening non-sense mutation with codon TGG coding for amino acid tryptophan substituted with TAG a non-sense codon at nucleotide No. 825 in exon 2 of synaptogyrin 1 gene of chromosome 22q11–13, thereby detecting pre-disposition to schizophrenia in a subset of patients and a method thereof.

11 Claims, 4 Drawing Sheets

FIGURE 4

Figure 1:
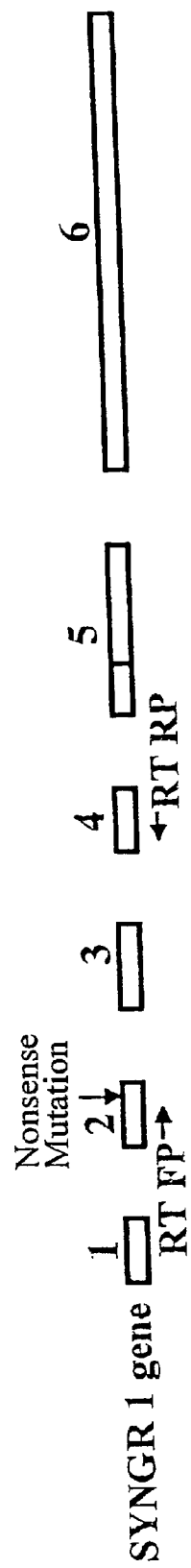

SEQ ID NO : 1 ttgaagcagc tggcccgaagt
SEQ ID NO : 2 tccccactct gagaccctga ac
SEQ ID NO : 3 acagaggtcg tgggtgag
SEQ ID NO : 4 agctggacag aggtcgtggg tgagctg
SEQ ID NO : 5 agctggacag aggtcgtggg tgagcta
SEQ ID NO : 6 gtcgtgggtg agctggagga gcaggcc
SEQ ID NO : 7 gtcgtgggtg agctagagga gcaggcc
SEQ ID NO : 8 ggcatgcctc cttggtctca
SEQ ID NO : 9 acatccgggc ctgctcctc

SEQUENCE LISTING

<160> NUMBER OF SEQ ID NOS: 9

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: primers for
      identifying and screening non-sense mutation in
      Schizophrenia

<400> SEQUENCE: 1
ttgaagcagc tggcccgaat gt                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: primers for
      identifying and screening non-sense mutation in
      Schizophrenia

<400> SEQUENCE: 2
tccccactct gagaccctga ac                                              22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: primers for
      identifying and screening non-sense mutation in
      Schizophrenia

<400> SEQUENCE: 3
acagaggtcg tgggtgagct                                                 20

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: primers for
      identifying and screening non-sense mutation in
      Schizophrenia

<400> SEQUENCE: 4
agctggacag aggtcgtggg tgagctg                                         27

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Primers for
      identifying and screening non-sense mutation in
      schizophrenia

<400> SEQUENCE: 5
agctggacag aggtcgtggg tgagcta                                         27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:: primers
      for identifying and screening non-sense mutation in
      Schizophrenia

<400> SEQUENCE: 6
gtcgtgggtg agctggagga gcaggcc                                         27

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:: primers
      for identifying and screening non-sense mutation in
      Schizophrenia

<400> SEQUENCE: 7
gtcgtgggtg agctagagga gcaggcc                                         27

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:  primers -continued

```
      for identifying and screening non-sense mutation in
      schizophrenia

<400> SEQUENCE: 8
ggcatgcctc cttggtctca                                              20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: primers for
      identifying and screening non-sense mutation in
      Schizophrenia

<400> SEQUENCE: 9
acatccgggc ctgctcctc                                               19
```

PRIMERS FOR SCREENING SCHIZOPHRENIA AND A METHOD THEREOF

FIELD OF THE INVENTION

The present invention relates to novel primers useful for identifying and screening non-sense mutation with codon TGG coding for amino acid tryptophan substituted with TAG, a non-sense codon, at nucleotide No. 825 in exon 2 of synaptogyrin 1 gene of chromosome 22q11–13. thereby detecting pre-disposition to schizophrenia in a subset of patients and a method thereof.

BACKGROUND AND PRIOR ART REFERENCES

Schizophrenia is a common and devastating illness afflicting at least 1% of the population worldwide. The characteristic symptoms involve disturbances in perception and inference (hallucinations and delusions), abnormalities in language, behaviour and motor function (disorganized speech, bizarre behaviour and catatonia) and deficits in emotional capacity and drive (affective flattening, anhedonia and avolition).

Abnormal neurotransmission affecting the dopamine, serotonin, glutamine, gamma-aminobutyric acid, and cholecystokinin systems have been reported in schizophrenia (Wolf et al, 1993). These abnormalities may affect genes involved in neurotransmitter metabolism, such as Catechol-o-methyl transferase (COMT) (Lachman et al, 1996) and Tyrosine hydroxylase (Ref); neurotransmitter receptors such as dopamine receptors (Seeman et al, 1993), N-methyl-D-Aspartate (NMDA) receptor (Nudmamud et al, 2001) and serotonin receptors (Chiu et al, 2001); and neurotransmitter transporters such as dopamine transporter (Persico et al, 1997).

Neurodevelopmental abnormalities are also strongly implicated in schizophrenia, with reports of defects in neuronal cytoskeleton (Arnold et al, 1991), neuronal cytoarchitecture (Arnold et al, 1997) and migration, cellular polarity, and synaptic pruning (Arnold, 1999). Thus, in schizophrenia, at least two processes appear to be aberrant: neurotransmission and neuronal development primarily affecting the later stages of synapse formation.

Unfortunately, there is no objective laboratory test for schizophrenia, and the diagnosis is made by clinical interview. Since there is a continuing need for developing diagnostic methods and new therapies for such diseases, efforts have been devoted to the characterization and elucidation of the genes responsible for schizophrenia.

In an attempt to device a method for diagnosing schizophrenia, Meloni et al (U.S. Pat. No. 6,210,879) used a microsatellite marker, HUMTH01 present in the first intron of tyrosine hydroxylase gene or finding association with schizophrenia This marker consists of repeated tetrameric TCAT motifs. The most frequently encountered allele of the marker comprises 10 repeated motifs and a deletion of one base pair in the fifth repeated motif, which has the sequence CAT. However, while doing association analysis of this repeat with schizophrenia, they observed that the perfect repeat (without the deletion) was rare and only present in schizophrenic patients.

Although, not much is known about the cause of schizophrenia, the disease has a strong genetic component. Research into the genetics of schizophrenia reveals that this disease is heterogeneous and is a "complex genetic" disease, that is, several genes may be involved in the etiology of this disease.

Several genetic studies have reported significant linkage to several chromosomal regions, which include 1q21–22, 6p24–22, 7q, 8p22–21, 10p14–13, 13q32, 18p and 22q11–13 (Riley and McGuffin, 2000).

One of the most intensively studied regions amongst these includes several loci on chromosome 22. Initial genome wide scans for schizophrenia by different groups suggested possible linkage for markers on chromosome 22q although neither of the groups reported statistically significant results (Schwab et al, 1999; Coon et al, 1994; Pulver et al, 1994).

A combined transmission disequilibrium and linkage analysis of D22S278 in 574 families further strengthened the possibility of a susceptibility locus on chromosome 22q (Schizophrenia Collaborative Linkage group for chromosome 22). A further line of evidence implicating chromosome 22 in schizophrenia has come from the study of patients with a congenital malformation called Velo Cardio Facial Syndrome (VCFS). VCFS is known to be caused by deletions in the region of 22q11.2-q11.23 and patients suffering from this disorder show a high prevalence of psychiatric illnesses including both bipolar disorder and schizophrenia (Arnold, 2001). Taken together, these independent lines of evidence from cytogenetic studies and linkage analysis studies suggest that chromosome 22 might indeed harbour susceptibility loci for schizophrenia.

Apart from linkage studies, an alternative approach which has evoked a great deal of interest in the recent years has been the study of trinucleotide repeat expansions in bipolar disorder and schizophrenia (Vincent et al, 2000). Studies of anonymous CAG repeats using the Repeat Expansion Detection (RED) technique have demonstrated expanded repeats in schizophrenia and bipolar disorder with considerable overlap between patients and controls (O'Donovan et al, 1996; Morris et al, 1995).

A great deal of effort has focused on the identification of loci containing trinucleotide repeats as candidate genes for these diseases. The candidate gene approach, however, has been unable to demonstrate large expansions of trinucleotide repeats in the range of those seen in tile diseases caused by triplet repeat expansions in patients suffering from schizophrenia and bipolar disorder (Vincent et al, 2000).

The failure to observe large expansions has led to suggestions that it might be worthwhile studying moderate trinucleotide repeat expansions in patients suffering from these diseases (Petronis et al, 1996).

Applicants have also proposed earlier that a difference in allele sizes or 'allele span' at such polymorphic trinucleotide repeat loci may also be implicated in bipolar disorder and schizophrenia (Saleem et al, 1998; Saleem et al, 2000).

As chromosome 22 has been repeatedly implicated in bipolar disorder and schizophrenia, susceptibility loci on this chromosome might contain expanded CAG repeats involved in the pathogenesis of these disorders. In order to identify such loci on chromosome 22, CAG repeals containing more than five repeats and mapping to schizophrenia susceptibility loci on chromosome 22 were identified and studied for the association with the disease. One of such CAG repeat markers, 22CH3, present on chromosome 22q11–13 was shown to be associated with schizophrenia in Indian population (Saleem et al, 2001). This locus is biallelic with 7 and 8 CAG repeats. The 8 repeat allele at this locus was significantly over represented in schizophrenic patients when compared to ethnically matched controls. The applicants further identified genes in the vicinity of this locus. Out of these, Synaptogyrin1 was chosen as a candidate gene for schizophrenia since it plays an integral role in neurotransmitter release, thus, mutations in this gene could explain many of the defects observed in schizophrenia.

Two recent studies have reported mutations in two different genes in schizophrenic patients. One of them is a frameshift mutation in KCNN3 gene, located on chromosome 1q21–22, Sound in only one schizophrenic patient (Bowen et al, 2001). The mutation found to be associated with schizophrenia is a missense mutation in WKL 1 gene, present on 22q11–13, and is shown to be segregating with schizophrenia in only one large family (Meyer et al, 2001). Since schizophrenia is a multigenic disorder, so it is quite possible that this region may harbour some other genes also, which when mutated might lead to schizophrenia.

In a study involving microarray expression profiling of prefrontal cortex from matched pairs of patients with schizophrenia and control subjects, it was found that transcripts encoding proteins involved in the regulation of presynaptic function were decreased in all subjects with schizophrenia (Mimics, 2000).

Further Double knockout mice for Synaptogyrin 1 and synaptophysin genes have shown deficits in long-term and short-term synaptic plasticity (Roger et al, 1999). These studies only suggest that Synaptogyrin 1 is a potential candidate gene for conferring susceptibility to schizophrenia.

The applicants have consequently examined the role of Synaptogyrin 1 gene in conferring susceptibility to schizophrenia in Indian population. The human SYNGR1 gene reveals three (SYNGR1a, SYNGR1b, SYNGR1c) alternative transcript forms of 4.5, 1.3 and 0.9 kb, respectively. The most abundant SYNGR1 a transcript, the 4.5-kb form, which corresponds to RATSYNGR1, is highly expressed in neurons of the central nervous system and at much lower levels in other tissues, as determined by in situ hybridization histochemistry. The levels of SYNGR1b and SYNGR1c transcripts are low and limited to heart, skeletal muscle, ovary and fetal liver (Kedra et al, 1997).

Schizophrenia is a multigenic disorder, so the identification of more candidate genes in addition to (hose already known is required for predicting the pre-disposition to schizophrenia rather than diagnosis only when the symptoms have already set in. This would help in devising life style changes and to have suitable environs for the subjects predisposed to the disease, which would be helpful in alleviating tile severity of schizophrenia.

Present invention relates to a method of identification of mutation in Synaptogyrin 1 gene for detection of pre-disposition to schizophrenia. Utility of the invention lies in the detection of mutation in Synaptogyrin 1 gene, which has been envisaged to be responsible for susceptibility to schizophrenia. The invention also has the utility for developing therapeutics for treatment of schizophrenia, as well as the constructions of transgenic animals expressing the mutant gene. A CAG repeat marker (22CH3) on chromosome 22q11–13 has been found to be associated with schizophrenia in the Indian population. In the vicinity of this region lies the Synaptogyrin 1 gene, which plays all integral role in neurotransmission. More particularly, the present invention relates to the method of identifying mutations in Synaptogyrin 1 gene. The present invention also provides the specific primers, which can be used for detecting mutation in Synaptogyrin 1 gene. The present invention also relates to methods for diagnosing and detecting carriers of the mutation in Synaptogyrin 1 gene.

OBJECT OF THE PRESENT INVENTION

The main object of the present invention is to develop probes and/or primers specific toward mutation sites of schizophrenic patients.

Another main object of the present invention is to develop a method to identify genetic mutations in schizophrenia.

Yet another object of the present invention is to develop a screening method for patients suffering from schizophrenia.

Still another object of the present invention is to develop oligonucleotide primers specific for amplification of mutations comprising DNA stretch of schizophrenic patients.

Still another object of the present invention is to determine the nature of mutations in schizophrenic patients.

Still another object of the present invention is to determine the location of the mutations in the human genome.

Still another object of the present invention is to identify mutations in schizophrenic patients of varied alleles.

Still another object of the present invention is to determine the inheritance pattern of schizophrenia in affected families.

Still another object of the invention is to confirm the functional implication of gene mutations of human brain tissue.

Still another object of the present invention is to develop a diagnostic kit for the identification of a pre-disposition to schizophrenia.

SUMMARY OF THE PRESENT INVENTION

The present invention relates to novel primers useful for identifying and screening a non-sense mutation with codon TGG coding for amino acid tryptophan substituted with TAG, a non-sense codon at nucleotide No. 825 in exon 2 of synaptogyrin 1 gene of chromosome 22q11–13, thereby detecting pre-disposition to schizophrenia in a subset of patients and a method thereof.

DETAILED DESCRIPTION OF THE PRESENT INVENTION

Accordingly, present invention relates to novel primers useful for identifying and screening non-sense mutation with codon TGG coding for amino acid tryptophan substituted with TAG, a non-sense codon, at nucleotide No. 825 in exon 2 of synaptogyrin 1 gene of chromosome 22q11–13, thereby detecting pre-disposition to schizophrenia in a subset of patients.

One embodiment of the present invention, is the primers of SEQ ID NO: 1 and 2.

Another embodiment of the present invention, is the primer of SEQ ID NO: 3.

Another embodiment of the present invention, is the primers and/or probes of SEQ ID NO: 4–7.

In still another embodiment of the present invention, said primers are used for amplifying exon 2 of synaptogyrin 1 gene.

In still another embodiment of the present invention, said primers are used for screening non-sense mutation of codon TGG coding for amino acid tryptophan substituted with TAG, a nonsense codon, at nucleotide No. 825 from 5' end in exon 2 in synaptogyrin 1 gene of chromosome 22q11–13.

In still another embodiment of the present invention, said primer is designed up to the penultimate position of said non-sense mutation.

In still another embodiment of the present invention, said primer has GC content ranging between 40–60%.

In still another embodiment of the present invention, said primers and/or probes are used for screening allelic variants of non-sense mutation of codon TGG coding for amino acid tryptophan substituted with TAG, a non-sense codon, at nucleotide No. 825 from 5' end in exon 2 in synaptogyrin 1 gene of chromosome 22q 11–13.

In still another embodiment of the present invention, wherein primers and/or probes of SEQ ID NO: 4 and 5 are designed to have a mutated base occupy the 3' position of the probe and/or primer of SEQ ID NO: 5.

In still another embodiment of the present invention, primers and/or probes of SEQ ID NO: 6 and 7 are designed to have mutated a base occupy the central position of the probe and/or primer of SEQ ID NO: 7.

Further embodiment of the present invention, a method of screening human beings for detection of pre-disposition to schizophrenia by identifying non-sense mutation of codon TGG coding for amino acid tryptophan substituted with TAG, a non-sense codon, at nucleotide No. 825 from 5' end in exon 2 and its allelic variants in synaptogyrin 1 gene of chromosome 22q11–13.

In still another embodiment of the present invention, said method comprises the step of isolating DNA from blood leukocytes.

In still another embodiment of the present invention, said method comprises the step of amplifying isolated DNA by PCR using primers of SEQ ID No. 1 and/or 2 of enclosed sequence listing, specific for exons of synaptogyrin 1 gene.

In still another embodiment of the present invention, said method comprises the step of sequencing the amplified DNA.

In still another embodiment of tile present invention, said method comprises the step of comparing the sequenced DNA with that of normal synaptogyrin 1 gene.

In still another embodiment of the present invention, said method comprises the step of identifying the said mutation.

In still another embodiment of the present invention, said method comprises the step of designing an oligonucleotide primer and/or probe of SEQ ID NO: 3 of the enclosed sequence listing, with its 3' end extending up to the penultimate position of said mutation.

In still another embodiment of the present invention, said method comprises the step of screening for said nonsense mutation using primer and/or probe of SEQ ID NO: 3.

In still another embodiment of the present invention, said method comprises the step of screening of said allelic variation for said non-sense mutation using appropriate allele specific oligonucleotide probes and/or primers selected from a group comprising SEQ ID NO: 4 to 7 of the enclosed sequence listing.

In still another embodiment of the present invention, said method comprises the step of using said method to understand the inheritance pattern in schizophrenic families.

In still another embodiment of the present invention, said method comprises the step of achieving early detection in order to help manage the disease before physiological manifestation sets in.

In still another embodiment of the present invention, said method wherein affected individuals with said mutation are in heterozygous state.

A further embodiment of the present invention is a diagnostic kit useful for screening human beings for detection of pre-disposition to schizophrenia, said kit comprising primers of SEQ ID NO: 1–2, and probes and/or primers of SEQ ID NO. 3–7, and other additives selected from restriction enzymes, reverse transcriptases, polymerases, ligases, linkers, nucleoside triphosphates as substrate, suitable buffers, labels, and/or other accessories and thereby identifying non-sense mutation of codon TGG coding for amino acid tryptophan substituted with TAG a non-sense codon at nucleotide No. 825 from 5' end in exon 2 and its allelic variants in synaptogyrin 1 gene of chromosome 22q11–13.

Another embodiment of the present invention is said kit, wherein probes are optionally immobilized on said substrate.

Another embodiment of the present invention is said kit, wherein restriction enzymes are selected from a group comprising HpaII, HaeIII, BumHI, HpaI, EcoRI, HindIII, and PvuII.

Another embodiment of the present invention is said kit, wherein linkers are selected from both sticky and blunt end types.

Another embodiment of the present invention is said kit, wherein nucleotide triphosphates are selected from a group comprising adenine triphosphates, guanine triphosphates, cytosine triphosphates, and thymine triphosphates.

In still another embodiment of the present invention, direct sequencing of exons of this gene in the patient samples led to the discovery of nonsense mutation in second exon in one schizophrenic family. In the affected individuals of this family the codon TGG, which codes for amino acid tryptophan has been mutated to TAG, which is a nonsense codon.

In still another embodiment of the present invention the mutation was present in the heterozygous state in the affected individuals, which could lead to the haploinsufficiency of the Synaptogyrin 1 gene product.

Since Synaptogyrin 1 is involved in neurotransmission, a nonsense mutation in this gene might lead to a susceptibility to schizophrenia. Further genotyping of 148 schizophrenic probands and 143 ethnically matched normal controls did not show this mutation. These results constitute the first demonstration of association of a nonsense mutation in a candidate gene, conferring susceptibility to schizophrenia.

A subset of the schizophrenia patients may harbor this mutation or yet unknown mutation in this gene, as it is often found that many different mutations localize to a given gene whose loss of function is responsible for the disease in a subset of patients.

The expression of exon 2 of Synaptogyrin 1 gene in brain is confirmed by amplifying the region spanning the nonsense mutation in brain cDNA using exon 2 and exon 4 specific primers of SEQ IDs NO: 8 and 9.

5' GGC ATG CCT CCT TGG TCT CA 3' (As listed in SEQ ID NO: 8)

5' CGT CCG TCC CTT CGT TCA 3' (As listed in SEQ ID NO: 9)

In an embodiment of the present invention, the primers of the provided method suitable for amplifying exon 2 of Synaptogyrin 1 gene containing nonsense mutation are selected from the group consisting of SEQ ID NO: 1, SEQ ID NO: 2 and the compliments thereof.

In another embodiments the allele specific primers and probes of method useful for detection of nonsense mutation in Synaptogyrin 1 gene are selected from the group consisting of SEQ ID NO: 4, SEQ ID NO: 5, SEQ ID NO: 6, SEQ ID NO: 7 (wherein the mutated base occupies a central position of the probe).

In an embodiment to tile present invention, the length of the oligonucleotide primers and probes are in the range of 5 to 100 bases.

In an embodiment to the present invent ions the diagnostic kit for the detection of nonsense mutation (TGG to TAG) may comprise of suitable primers and probes selected from the group of sequences—SEQ ID NO: 1 to 9.

In still another embodiment of the present invention, applicants carried out the PCR amplification of exon 2 of the human Synaptogyrin 1 gene using oligonucleotide primers.

These primers were designed in accordance with the human Synaptogyrin 1 sequence submitted by Sanger Centre, Hinxton, Cambridgeshire, CB10 1SA, and UK. (8 Dec. 1999) (GenBank accession number—AL022326).

In still another embodiment of the present invention, the sequencing of the purified PCR product revealed nonsense mutation in exon 2 of human Synaptogyrin 1 gene in one schizophrenic family. It was apparent, therefore, that there is a hitherto unrecognized allele or subtype of the human Synaptogyrin 1 gene.

Another embodiment of the present invention provides a sequence for the allelic variants of human Synaptogyrin 1 gene comprising nonsense mutation, compared with the human Synaptogyrin 1 gene sequence in the database (GenBank accession number—AL022326).

TABLE 1

| Site of change | Base change | Amino-acid alteration |
|---|---|---|
| 825 | G-A | Trp-nonsense codon |

In still another embodiment of the present invention, the sites of changes are in accordance with the PCR Product Sequence obtained using primers SEQ ID NO: 1 and 2 flanking exon 2 of Synaptogyrin 1 gene.

In still another embodiment of the present invention, the mutated site had either G or A. The substitution G→A changes amino acid tryptophan to nonsense codon which consequently leads the nucleotide sequence of the allelic variant of human Synaptogyrin 1 gene containing the nonsense mutation.

Another embodiment of the present invention is a PCR Product Sequence using primers SEQ ID NO: 1 and 2 flanking exon 2 of Synaptogyrin 1 gene.

In still another embodiment of the present invention, applicants carried out the PCR amplification of exon 2 of the human Synaptogyrin 1 gene using oligonucleotide primers. These primers were designed in accordance with the human Synaptogyrin 1 sequence submitted by Sanger Centre, Hinxton, Cambridgeshire, CB10 1SA, and UK. (8 Dec. 1999) (GenBank accession number—AL022326).

The mutated site is at nucleotide position 825 in the said gene sequence.

In still another embodiment of the present invention, analysis of 20 densely affected schizophrenia families of South Indian origin as well as ethnically matched normal individuals revealed the presence of this non-sense mutation in one of the schizophrenic families. This family comprises of three schizophrenic patients in two normal individuals. Out of these, the nonsense mutation is present in heterozygous state in all three schizophrenic patients as well as in one of the normal individuals, and it is absent in the other normal individual. The normal individual having the mutation may be asymptomatic at present as she is of younger age, or this could be due to incomplete penetrance of the mutation. Further genotyping of 148 schizophrenic patients and 143 ethnically matched normal controls did not show this mutation.

In still another embodiment of the present invention, to demonstrate the expression of exon2 (containing the nonsense mutation) in human brain, the applicants designed the exon 2 and exon 4 specific primers, isolated RNA from human brain, made cDNA and amplified the region spanning the nonsense mutation in human brain cDNA. The exon 2 containing the nonsense mutation was found to be expressed in brain.

Anther embodiment of the present invention is a diagnostic kit comprising at least one or more allele-specific oligonucleotide as described in SEQ ID 1 to 9. Often, the kits contain one or more pairs of allele-specific oligonucleotides hybridizing to different forms of a polymorphism. In some kits, the allele-specific oligonucleotides are provided immobilized to a substrate, which can be used to detect mutation in Synaptogyrin 1 gene. Optional additional components of the kit include, for example, restriction enzymes, reverse-transcriptase or polymerase, the substrate nucleoside triphosphates, means used to label (for example, an avidin enzyme conjugate and enzyme substrate and chromogen if the label is biotin), and the appropriate buffers for reverse transcription, PCR, or hybridization reactions. Usually, the kit also contains instructions for carrying out the methods and also any other SNP detection reagent and method like TAQMAN®.

BRIEF DESCRIPTIONS OF THE ACCOMPANYING DRAWINGS

FIG. 1 shows schematic representation of the nonsense mutation in Synaptogyrin 1 gene. The top line depicts the position of the 6 exons of the Synaptogyrin 1 gene with the relative positions of nonsense mutation in the second exon, and the primers used for RT-PCR.

Figure 2:
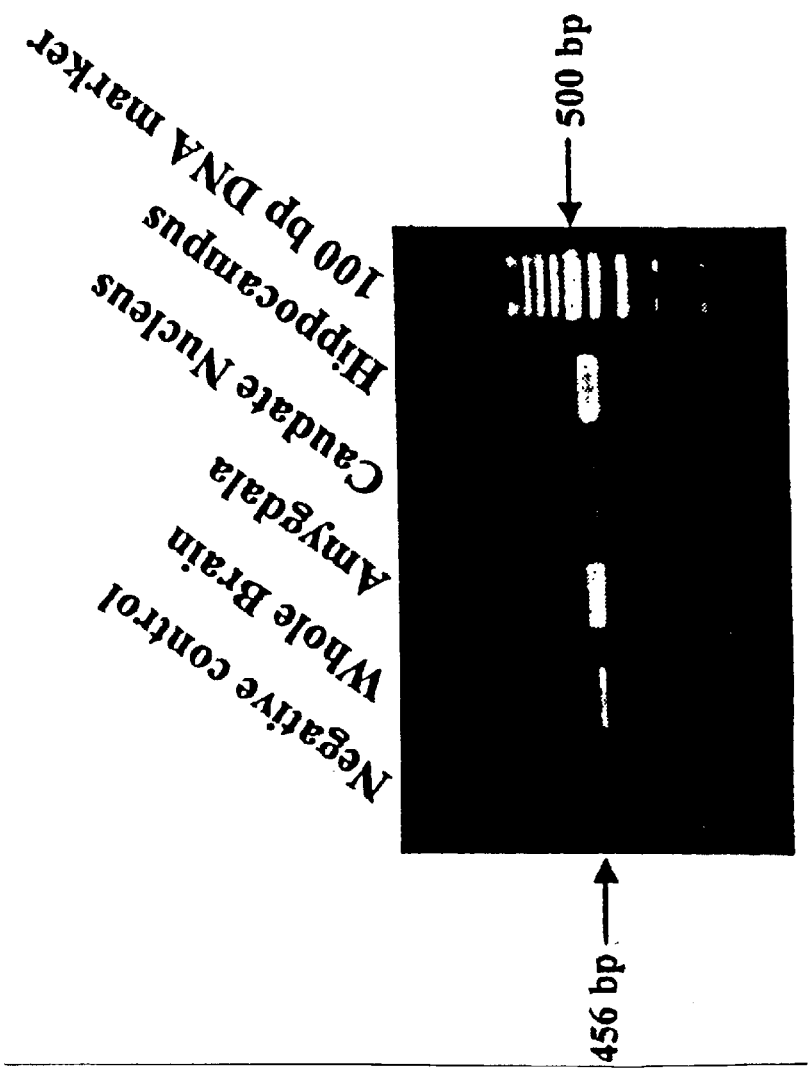

FIG. 2 shows the expression of exon 2 of Synaptogyrin 1 gene in different parts of brain by RT-PCR using exon 2 (SEQ ID NO: 8) and exon 4 (SEQ ID NO: 9) specific primers.

Figure 3:
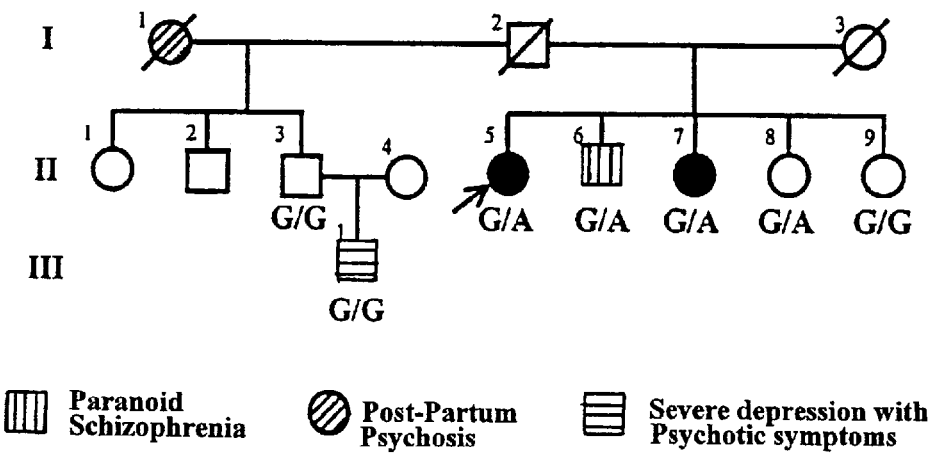
Figure 3:
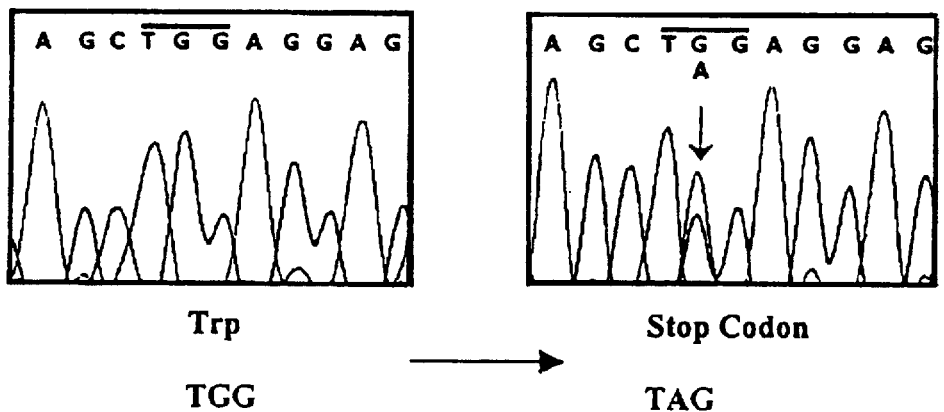

FIG. 3 shows the pedigree of the family in which the mutation has been found. The circles represent female members and squares represent male members. Filled circles and squares represent affected members of the family while open ones represent the normal family members. The horizontal line represents the marriage and the vertical line represent the next generation. The genotype of family members screened for the mutation is shown below the symbols. Below the pedigree is shown the electropherogram depicting the mutation in exon 2 of Synaptogyrin 1 gene.

FIG. 4 shows SEQ ID NO: 1 to 9.

The following examples are given by way of illustration of the present invention and should be construed to limit the scope of the present invention.

EXAMPLE 1

Identification of Nonsense Mutation in Synaptogyrin 1 Gene

This example describes the identification of mutation in exon 2 of Synaptogyrin 1 gene by PCR and sequencing, using certain oligonucleotide primers according to the invention. DNA was extracted from human peripheral blood leukocytes using a modification of the salting out procedure. The concentration of the DNA was determined by measuring the absorbance of the sample, at a wavelength of 260 nm. The DNA from schizophrenic probands was then amplified by polymerase chain reaction by using the oligonucleotide primer 1 and 2 (SEQ ID NO: 1 and 2). The samples were denatured at 94° C. for 5 min followed by 35 cycles of denaturation (94° C., 30sec), annealing (67° C., 30sec), extension (72° C., 1 min) and a final extension of 7 min at 72° C. in a Perkin Elmer Gene Amp PCR System 9600. This reaction produced a DNA fragment of 1057 bp. The PCR product was purified from band excised from agarose gel using a DNA ISOLATION KIT (Biological Industries, Israel) and both the strands of the PCR product were directly sequenced using dye terminator chemistry on an ABI Prism 377 automated DNA sequencer. The PCR product was shown to be identical to the exon 2 of the Synaptogyrin 1 gene sequence in the database (accession number—AL022326), except for the previously mentioned mutation in one schizophrenic patient.

EXAMPLE 2

Screening Mutation in the Population

This example describes a primer extension reaction used to screen single nucleotide variants. The DNA samples from 148 patients and 143 normal subjects were amplified by PCR and the PCR products were purified as described in example 1. The primer extension reaction was performed on the purified PCR products using oligonucleotide primer and SNaPshot ddNTP primer extension kit (PE Biosystems). The oligonucleotide primer was designed till the penultimate position of mutation and the primer is extended by one. ddNTP, which is in accordance with the variant allele present. The reaction was performed for 25 cycles of denaturation (96° C., 10 sec), annealing (50° C., 5 sec) and extension (60° C., 30 sec) in a Perkin Elmer GeneAmp PCR System 9600. The primer extension products were treated with calf intestine alkaline phosphatase (New England Biolabs) for removing unincorporated dideoxynucleotides. The products were run on an ABI Prism 377 automated DNA sequencer. Depending on the color of the fluoroscently labeled dideoxynucleolide incorporated, the wild-type and mutant alleles of the Synaptogyrin gene were detected.

EXAMPLE 3

Nucleotide Sequence of Allelic Variants of Synaptogyrin 1 Gene

The nucleotide sequence of the allelic variant of Synaptogyrin 1 gene was derived using the method as described in example 1.

EXAMPLE 4

The Nonsense Mutation is Segregated Along with Disease in Schizophrenic Family

The nonsense mutation was found in the affected members of one schizophrenic family. This family comprises &f three schizophrenic patients and two normal individuals. Out of these, the nonsense mutation is present in heterozygous state in all three schizophrenic patients as well as in one normal individual, and it is absent in the other normal individual. The normal individual having the mutation may be asymptomatic at present as she is of younger age. This could also be due to incomplete penetrance of the mutation.

EXAMPLE 5

Studying the Expression of Exon 2 of Synaptogyrin 1 Gene in Human Brain

To demonstrate the expression of exon2 (containing nonsense mutation) in human brain, the exon 2 and exon 4 specific primers were designed. RNA was isolated from human brain using, EZ RNA Isolation kit (Biological Industries). cDNA was synthesized using random primers and oligo dT primers (1st strand cDNA synthesis kit for RT-PCR, Boehringer Mannheim). The region spanning the nonsense mutation in human brain cDNA was amplified using the exon 2 and exon 4 specific primers. The exon 2 containing the nonsense mutation was found to be expressed in brain.

---

What is claimed is:

1. The primers of SEQ ID NO: 1 and 2 useful for screening human beings for a pre-disposition to schizophrenia.

2. The primer of SEQ ID NO: 3 useful for screening human beings for a pre-disposition to schizophrenia.

3. The primers and/or probes of SEQ ID NO: 4–7 useful for screening human beings for a pre-disposition to schizophrenia.

4. A method of screening human beings for a pre-disposition to schizophrenia by identifying non-sense mutation of codon TGG coding for amino acid tryptophan substituted with TAG, a non-sense codon, at nucleotide No. 825 from 5' end in exon 2 and its allelic variants in synaptogyrin 1 gene of chromosome 22q11–13, said method comprising:
  (a) isolating DNA from blood leukocytes,
  (b) amplifying isolated DNA by PCR using primers of SEQ ID NO: 1 and/or 2 of enclosed sequence listing, specific for exons of synaptogyrin 1 gene,
  (c) sequencing the amplified DNA,
  (d) comparing the sequenced DNA with that of normal synaptogyrin 1 gene,
  (e) identifying the said mutation,
  (f) designing oligonucleotide primer and/or probe of SEQ ID NO: 3 of enclosed sequence listing with its 3' end extending up to penultimate position of said mutation,
  (g) screening for said non-sense mutation using primer and/or probe of step (f), and
  (h) screening of said allelic variation for said non-sense mutation using appropriate allele specific oligonucleotide probes and/or primers selected from the group consisting of SEQ ID NO: 4 to 7 of enclosed sequence listing.

5. A method as claimed in claim 4, wherein said method is used to understand an inheritance pattern in schizophrenic families.

6. A method as claimed in claim 4, wherein affected individuals with said mutation are in heterozygous state.

7. A diagnostic kit useful for screening human beings for detection of pre-disposition to schizophrenia by identifying non-sense mutation of codon TGG coding for amino acid tryptophan substituted with TAG a non-sense codon at nucleotide No. 825 from 5' end in exon 2 and its allelic variants in synaptogyrin 1 gene of chromosome 22q11–13, said kit comprising primers of SEQ ID NO: 1–2, and probes and/or primers of SEQ ID NO: 3–7, and other additives selected from restriction enzymes, reverse transcriptases, polymerases, ligases, linkers, nucleoside triphosphates as substrate, suitable buffers, labels, and/or other accessories.

8. A kit as claimed in claim 7, wherein probes are optionally immobilized on said substrate.

9. A method as claimed in claim 4, wherein primers and or probes of SEQ ID NO: 4 and 5 are designed to have a mutated base occupying the 3' position of the probe and/or primer of SEQ ID NO: 5.

10. A method as claimed in claim 4, wherein primers and or probes of SEQ ID NO: 6 and 7 are designed to have a mutated base occupying the central position of the probe and/or primer of SEQ ID NO: 7.

11. A method as claimed in claim 4, wherein early detection of a predisposition to schizophrenia can be made before physiological manifestation sets in by identifying nonsense mutation of codon TGG by using primers of SEQ ID NO: 1–7.

* * * * *